United States Patent
McKay

(10) Patent No.: US 8,177,848 B2
(45) Date of Patent: *May 15, 2012

(54) OSTEOGENIC FUSION DEVICE

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/800,461

(22) Filed: May 14, 2010

(65) Prior Publication Data

US 2010/0234953 A1    Sep. 16, 2010

Related U.S. Application Data

(60) Continuation of application No. 11/214,412, filed on Aug. 29, 2005, now Pat. No. 7,763,079, which is a continuation of application No. 10/634,711, filed on Aug. 5, 2003, now Pat. No. 7,179,293, which is a division of application No. 09/581,335, filed as application No. PCT/US98/26254 on Dec. 10, 1998, now Pat. No. 6,648,916, which is a continuation-in-part of application No. 08/988,142, filed on Dec. 10, 1997, now Pat. No. 6,146,420.

(51) Int. Cl.
*A61F 2/44* (2006.01)
(52) U.S. Cl. .................................................... 623/17.16
(58) Field of Classification Search .... 623/17.11–17.16, 623/16.11; 606/246–249
See application file for complete search history.

(56) References Cited

U.S. PATENT DOCUMENTS

| | | |
|---|---|---|
| 3,867,728 A | 2/1975 | Stubstad et al. |
| 4,375,810 A | 3/1983 | Belykh et al. |
| 4,501,269 A | 2/1985 | Bagby |
| 4,863,476 A | 9/1989 | Shepperd |
| 4,878,915 A | 11/1989 | Brantigan |
| 4,919,666 A | 4/1990 | Buchhorn et al. |

(Continued)

FOREIGN PATENT DOCUMENTS

DE    4409836 A    9/1995

(Continued)

*Primary Examiner* — Alvin J Stewart

(57) ABSTRACT

An interbody osteogenic fusion device is provided that includes opposite end pieces with an integral central element. The end pieces are sized to maintain the height of an intervertebral disc space. The central element has a much smaller diameter so that the osteogenic fusion device forms an annular pocket around the central element. An osteogenic material is disposed within the annular pocket between the opposite end pieces. In one embodiment, the osteogenic material constitutes a collagen sheet soaked in a solution containing a bone morphogenetic protein. The osteogenic fusion device is configured so that the osteogenic material is in direct contact with the adjacent vertebral bone. In addition to the enhanced area of contact between the vertebral bone and the fusion material, the inventive osteogenic fusion device reduces stress-shielding and minimizes the radiopacity of the implant so that growth of the fusion mass can be continuously assessed. In yet another embodiment, the osteogenic fusion device includes at least one end piece with a truncated surface. The osteogenic fusion devices of the present invention may be combined with other fusion devices to form an implant system. The implant system includes at least one load bearing member having a truncated surface configured to nest within another load bearing member, preferably the load bearing, osteogenic fusion device of the present invention. The invention also provides implant systems comprising adjacent load bearing members connected to one another to resist lateral separation. Methods of promoting fusion bone growth in the space between adjacent vertebrae utilizing devices and systems of the invention are also described.

15 Claims, 7 Drawing Sheets

U.S. PATENT DOCUMENTS

| | | | |
|---|---|---|---|
| 4,961,740 A | 10/1990 | Ray et al. | |
| 5,015,247 A | 5/1991 | Michelson | |
| 5,026,373 A | 6/1991 | Ray et al. | |
| 5,055,104 A | 10/1991 | Ray | |
| 5,059,193 A | 10/1991 | Kuslich | |
| 5,141,510 A | 8/1992 | Takagi et al. | |
| 5,171,278 A | 12/1992 | Pisharodi | |
| 5,207,710 A | 5/1993 | Chu et al. | |
| 5,219,363 A | 6/1993 | Crowninshield et al. | |
| 5,258,029 A | 11/1993 | Chu et al. | |
| 5,298,254 A | 3/1994 | Prewett et al. | |
| 5,336,223 A * | 8/1994 | Rogers | 606/258 |
| 5,348,026 A | 9/1994 | Davidson | |
| 5,360,430 A | 11/1994 | Lin | |
| 5,390,683 A | 2/1995 | Pisharodi | |
| 5,397,364 A | 3/1995 | Kozak et al. | |
| 5,423,816 A | 6/1995 | Lin | |
| 5,423,817 A | 6/1995 | Lin | |
| 5,433,718 A | 7/1995 | Brinker | |
| 5,443,515 A | 8/1995 | Cohen et al. | |
| 5,520,923 A | 5/1996 | Tjia et al. | |
| 5,554,191 A * | 9/1996 | Lahille et al. | 623/17.11 |
| 5,571,184 A | 11/1996 | DeSatnick | |
| 5,584,877 A | 12/1996 | Miyake et al. | |
| 5,584,880 A | 12/1996 | Martinez | |
| 5,593,409 A | 1/1997 | Michelson | |
| 5,618,286 A | 4/1997 | Brinker | |
| 5,645,598 A | 7/1997 | Brosnahan, III | |
| 5,653,763 A | 8/1997 | Errico et al. | |
| 5,665,122 A | 9/1997 | Kambin | |
| 5,676,699 A | 10/1997 | Gogolewski et al. | |
| 5,683,465 A * | 11/1997 | Shinn et al. | 623/17.14 |
| 5,693,100 A * | 12/1997 | Pisharodi | 623/17.16 |
| 5,766,252 A | 6/1998 | Henry et al. | |
| 5,766,253 A | 6/1998 | Brosnahan, III | |
| 5,776,199 A | 7/1998 | Michelson | |
| 5,860,977 A | 1/1999 | Zucherman et al. | |
| 5,885,287 A | 3/1999 | Bagby | |
| 5,980,522 A * | 11/1999 | Koros et al. | 623/17.11 |
| 6,015,436 A * | 1/2000 | Schonhoffer | 623/17.16 |
| 6,068,630 A | 5/2000 | Zucherman et al. | 606/249 |
| 6,102,950 A | 8/2000 | Vaccaro | |
| 6,123,705 A | 9/2000 | Michelson | |
| 6,146,420 A * | 11/2000 | McKay | 623/17.16 |
| 6,156,038 A * | 12/2000 | Zucherman et al. | 606/249 |
| 6,176,882 B1 * | 1/2001 | Biedermann et al. | 623/17.15 |
| 6,296,665 B1 * | 10/2001 | Strnad et al. | 623/17.16 |
| 6,302,914 B1 * | 10/2001 | Michelson | 623/17.16 |
| 6,306,170 B2 | 10/2001 | Ray | |
| 6,582,468 B1 * | 6/2003 | Gauchet | 623/17.16 |
| 6,648,916 B1 | 11/2003 | McKay | |
| 6,726,722 B2 * | 4/2004 | Walkenhorst et al. | 623/17.16 |
| 6,761,738 B1 * | 7/2004 | Boyd | 623/17.11 |
| 6,821,298 B1 * | 11/2004 | Jackson | 623/17.15 |
| 6,960,232 B2 * | 11/2005 | Lyons et al. | 623/17.16 |
| 7,018,415 B1 | 3/2006 | McKay | |
| 7,179,293 B2 * | 2/2007 | McKay | 623/17.11 |
| 7,201,775 B2 * | 4/2007 | Gorensek et al. | 623/17.11 |
| 7,285,135 B2 * | 10/2007 | McKay et al. | 623/17.16 |
| 7,481,839 B2 * | 1/2009 | Zucherman et al. | 623/17.11 |
| 7,537,616 B1 | 5/2009 | Branch et al. | |
| 7,618,460 B2 * | 11/2009 | Boyd | 623/17.16 |
| 7,763,079 B2 * | 7/2010 | McKay | 623/17.16 |
| 2001/0049560 A1 | 12/2001 | Paul et al. | |
| 2002/0116065 A1 | 8/2002 | Jackson | |
| 2005/0187626 A1 | 8/2005 | McKay et al. | |
| 2006/0004450 A1 | 1/2006 | McKay | |
| 2009/0138087 A1 * | 5/2009 | Miglietta et al. | 623/17.16 |
| 2009/0171390 A1 * | 7/2009 | Sankaran | 606/246 |
| 2010/0145463 A1 * | 6/2010 | Michelson | 623/17.16 |

FOREIGN PATENT DOCUMENTS

| | | |
|---|---|---|
| DE | 19630256 | 1/1998 |
| EP | 0577179 A | 1/1994 |
| EP | 0732093 A | 9/1996 |
| FR | 2712486 A | 5/1995 |
| WO | WO 91/06266 A | 5/1991 |
| WO | WO 91/11148 | 8/1991 |
| WO | WO 92/14423 | 9/1992 |
| WO | WO 94/07441 | 4/1994 |
| WO | WO 95/00082 | 1/1995 |
| WO | WO 95/17861 A | 7/1995 |
| WO | WO 95/25483 | 9/1995 |
| WO | WO 95/25485 A | 9/1995 |
| WO | WO 96/40014 | 12/1996 |
| WO | WO 97/23174 A | 7/1997 |
| WO | WO 98/04217 A | 2/1998 |

* cited by examiner

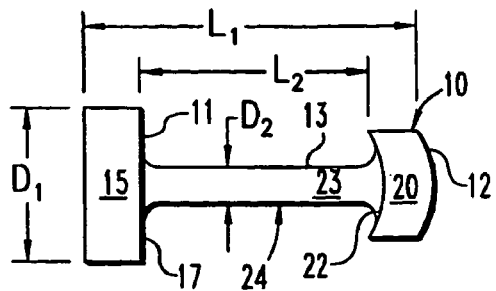
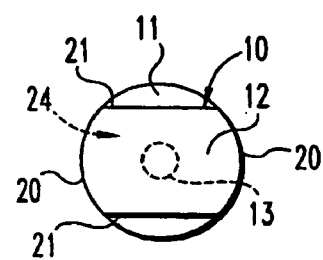
Fig. 1  Fig. 2
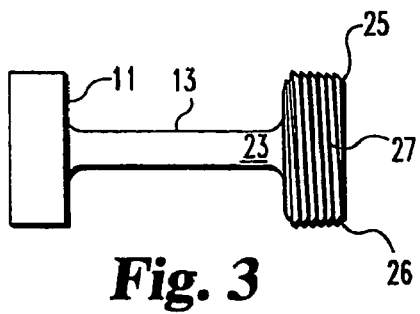
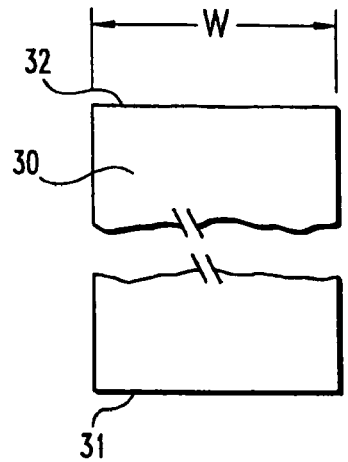
Fig. 3  Fig. 6
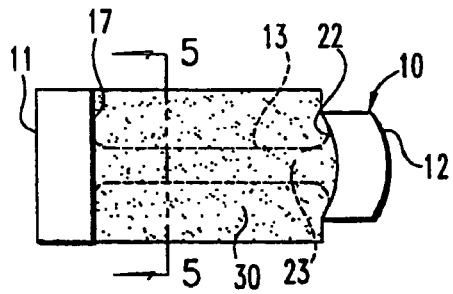
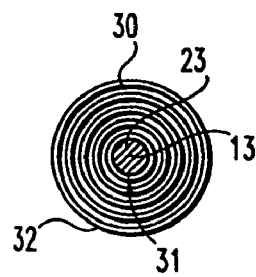
Fig. 4  Fig. 5
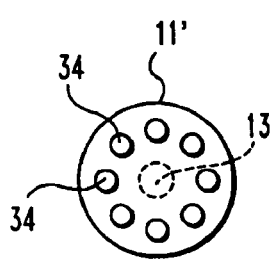
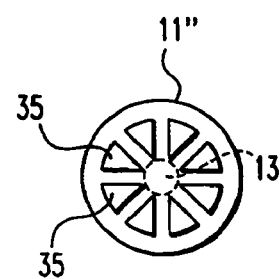
Fig. 7  Fig. 8

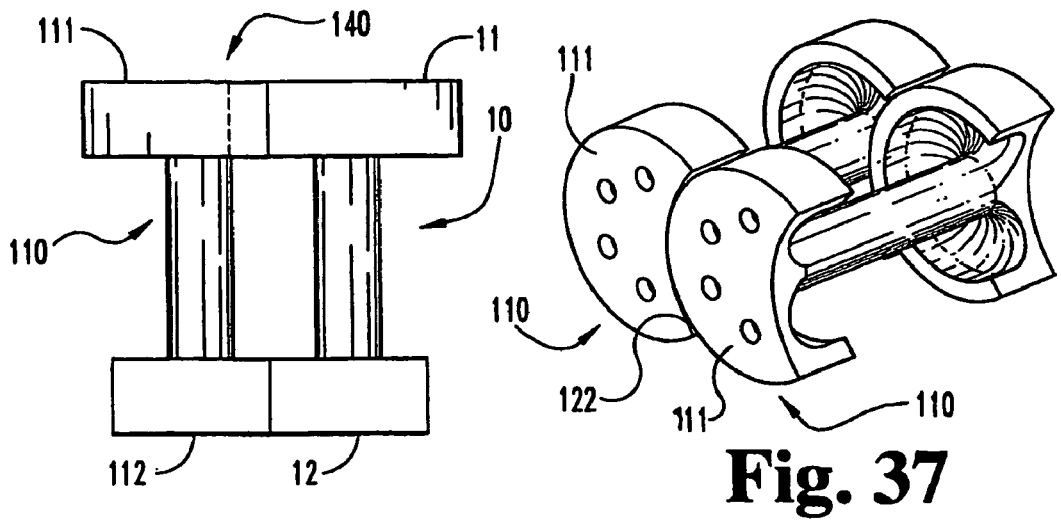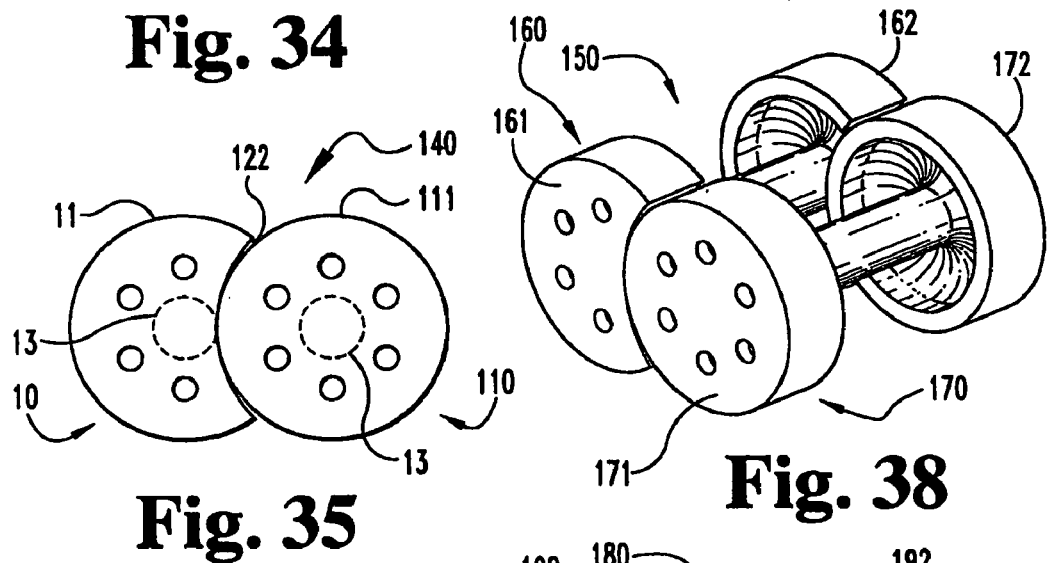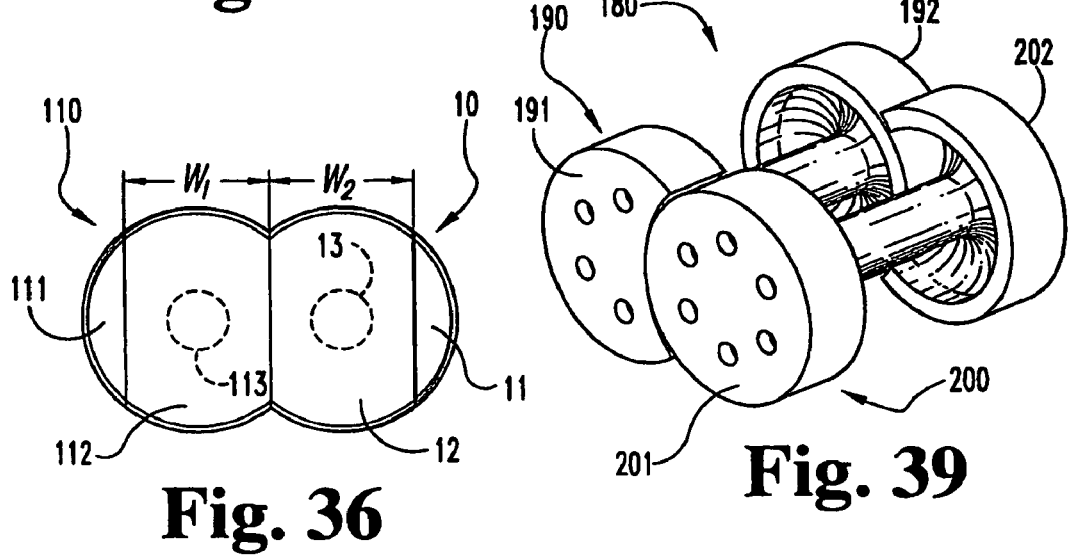

OSTEOGENIC FUSION DEVICE

CROSS REFERENCE TO RELATED APPLICATIONS

This application is a continuation of U.S. patent application Ser. No. 11/214,412, filed Aug. 29, 2005 now, U.S. Pat. No. 7,763,079, which is a continuation of U.S. patent application Ser. No. 10/634,711, filed Aug. 5, 2003 and issued as U.S. Pat. No. 7,179,293, which is a divisional of U.S. patent application Ser. No. 09/581,335, filed Sep. 25, 2000 and issued as U.S. Pat. No. 6,648,916, which is the National Stage of International PCT Application No. PCT/US98/26254, filed Dec. 10, 1998 and published in English, which is a continuation-in-part of U.S. patent application Ser. No. 08/988,142, filed Dec. 10, 1997 and issued as U.S. Pat. No. 6,146,420, all of which are hereby incorporated by reference in their entirety.

BACKGROUND OF THE INVENTION

The present invention relates to an implant to be placed into the intervertebral space left after the removal of a damaged spinal disc. Specifically, the invention concerns an osteogenic fusion device that enhances arthrodesis or fusion between adjacent vertebrae while also maintaining the normal spinal anatomy at the instrumented vertebral level.

In many cases, low back pain originates from damages or defects in the spinal disc between adjacent vertebrae. The disc can be herniated or can be affected by a variety of degenerative conditions. In many cases, these pathologies affecting the spinal disc can disrupt the normal anatomical function of the disc. In some cases, this disruption is significant enough that surgical intervention is indicated.

In one such surgical treatment, the affected disc is essentially removed and the adjacent vertebrae are fused together. In this treatment, a discectomy procedure is conducted to remove the disc nucleus while retaining the annulus. Since the disc material has been removed, a body must be placed within the intervertebral space to prevent the space from collapsing.

In early spinal fusion techniques, bone material, or bone osteogenic fusion devices, were simply disposed between adjacent vertebrae, typically at the posterior aspect of the vertebrae. In the early history of these osteogenic fusion devices, the osteogenic fusion devices were fanned of cortical-cancellous bone which was not strong enough to support the weight of the spinal column at the instrumented level. Consequently, the spine was stabilized by way of a plate or a rod spanning the affected vertebrae. With this technique, once fusion occurred across and incorporating the bone osteogenic fusion device, the hardware used to maintain the stability of the spine became superfluous.

Following the successes of the early fusion techniques, focus was directed to modifying the device placed within the intervertebral space. Attention was then turned to implants, or interbody fusion devices, that could be interposed between the adjacent vertebrae, maintain the stability of the disc interspace, and still permit fusion or arthrodesis. These interbody fusion devices have taken many forms. For example, one prevalent form is a cylindrical hollow implant or "cage". The outer wall of the cage creates an interior space within the cylindrical implant that is filled with bone chips, for example, or other bone growth-inducing material. Implants of this type are represented by the patents to Bagby, No. 4,501,269; Brantigan, No. 4,878,915; Ray, No. 4,961,740; and Michelson, No. 5,015,247. In some cases, the cylindrical implants included a threaded exterior to permit threaded insertion into a tapped bore formed in the adjacent vertebrae. Alternatively, some fusion implants have been designed to be impacted into the intradiscal space.

Experience over the last several years with these interbody fusion devices has demonstrated the efficacy of these implants in yielding a solid fusion. Variations in the design of the implants have accounted for improvements in stabilizing the motion segment while fusion occurs. Nevertheless, some of the interbody fusion devices still have difficulty in achieving a complete fusion, at least without the aid of some additional stabilizing device, such as a rod or plate. Moreover, some of the devices are not structurally strong enough to support the heavy loads and bending moments applied at certain levels of the spine, namely those in the lumbar spine.

Even with devices that do not have these difficulties, other less desirable characteristics exist. Recent studies have suggested that the interbody fusion implant devices, or cages as they are frequently called, lead to stress-shielding of the bone within the cage. It is well known that bone growth is enhanced by stressing or loading the bone material. The stress-shielding phenomenon relieves some or all of the load applied to the material to be fused, which can greatly increase the time for complete bone growth, or disturb the quality and density of the ultimately formed fusion mass. In some instances, stress-shielding can cause the bone chips or fusion mass contained within the fusion cage to resorb or evolve into fibrous tissue rather than into a bony fusion mass.

A further difficulty encountered with many fusion implants is that the material of the implant is not radiolucent. Most fusion cages are formed of metal, such as stainless steel, titanium or porous tantalum. The metal of the cage shows up prominently in any radiograph (x-ray) or CT scan. Since most fusion devices completely surround and contain the bone graft material housed within the cage, the developing fusion mass within the metal cage between the adjacent vertebrae cannot be seen under traditional radiographic visualizing techniques and only with the presence of image scatter with CT scans. Thus, the spinal surgeon does not have a means to determine the progress of the fusion, and in some cases cannot ascertain whether the fusion was complete and successful.

The field of spinal fusion can be benefited by an intervertebral fusion device that can support bone growth material within the intervertebral space, while still maintaining the normal height of the disc space. The device would beneficially eliminate the risk of stress-shielding the fusion mass, and would also provide for visualization of the fusion mass as the arthrodesis progresses.

SUMMARY OF INVENTION

To address the current needs with respect to interbody fusion devices, the present invention contemplates a osteogenic fusion device that is configured to place as much of the bone growth-inducing material as possible into direct contact with the adjacent bone. In one embodiment, the osteogenic fusion device includes an elongated body having opposite first and second end pieces separated by an integral central element. The central element has a significantly smaller diameter than the two end pieces. The osteogenic fusion device thus forms an annular pocket between the end pieces and around the central element.

In accordance with one aspect of the present invention, a bone growth-inducing material is disposed within the annular pocket around the central element of the osteogenic fusion device. In one specific embodiment, the bone growth-inducing material can constitute a sheet of a pharmaceutically suitable carrier for a bone growth factor, such as a bone morphogenetic protein. In this embodiment, the sheet can be a collagen sheet that is soaked with the BMP and then subsequently wrapped in spiral fashion around the central element of the osteogenic fusion device.

In one feature of the present invention, the osteogenic fusion device can be implanted in a bi-lateral approach. Specifically, two such osteogenic fusion devices can be inserted into prepared bores formed in the endplates of adjacent vertebrae after completion of a discectomy. The spinal loads are borne by the two end pieces that are in direct contact with the adjacent vertebral bodies. Preferably, the osteogenic fusion device has a length sufficient to allow the end pieces to at least partially contact the harder bone at the apophysis of the adjacent vertebrae. With the osteogenic fusion device thus inserted, the bone growth-inducing material is in direct contact with the adjacent vertebral bodies. In addition, bone growth-inducing material can be placed within the bi-lateral space separating the two osteogenic fusion devices. When fusion occurs, a substantial fusion mass is produced that is virtually uninterrupted by the material of the osteogenic fusion device itself.

Several alternative embodiments of the osteogenic fusion device are presented, all retaining the capability of supporting bone growth-inducing material so that it is in direct contact with the adjacent vertebrae. In some embodiments, additional elements of the central element are provided, while in another embodiment, an intermediate piece is provided for further support across the disc space. In one embodiment, osteogenic fusion devices are provided wherein at least one of the opposite end pieces includes a truncated surface. In yet another embodiment, the truncated surface advantageously includes opposite faces, such as opposite edges, that define an entrance to a cutout region. The cutout region is typically defined by the truncated surface and the truncated surface is preferably concave. Such implants are advantageously configured to nest within another fusion device, such as the fusion device of the present invention.

Another embodiment of the present invention provides an implant system including at least two load bearing members as described above adapted to be bilaterally placed between adjacent vertebrae, wherein at least one of the load bearing members has a truncated surface configured to nest within the other load bearing member.

Yet another embodiment of the invention provides an implant system for promoting fusion bone growth in the space between adjacent vertebrae which includes at least first and second load bearing members adapted to be bilaterally placed between adjacent vertebrae, wherein the load bearing members are connected to one another so as to resist lateral separation. In particular, a preferred embodiment provides a first of the load bearing members including a male member, and a second of the load bearing members including a female member. The male and female members cooperate to resist lateral separation of said devices. In another preferred embodiment, the load bearing members can be connected by a connecting member such as a plate spanning the two load bearing members.

In other embodiments of the invention, methods of promoting fusion bone growth in the space between adjacent vertebrae are provided. The methods include providing load bearing members or implant systems as described above, preparing adjacent vertebrae to receive the load bearing members or implant systems in an intervertebral space between adjacent vertebrae and placing the load bearing members or implant systems into the intervertebral space after the preparing step.

The present invention also contemplates an insertion tool and certain modifications to the osteogenic fusion device to accommodate the tool. In one preferred embodiment, the tool is essentially an elongated shank having opposite prongs extending therefrom. The prongs can engage truncated side walls of one of the end pieces. In addition, the opposite end piece can be formed with notches to receive the tips of the two prongs. With this design, the osteogenic fusion device can be a push-in or a threaded type osteogenic fusion device.

It is one object of the present invention to provide an interbody fusion device that allows the greatest possible contact between the adjacent vertebrae and the bone growth-inducing material supported by the osteogenic fusion device. It is a further object to provide such a osteogenic fusion device that is capable of supporting the loads generated throughout the spine without stress-shielding developing bone within the osteogenic fusion device.

Another object of the invention is achieved by features that minimize the radiopacity of the device. This results in a benefit to the surgeon of being able to more readily assess the progress of a spinal fusion.

Yet another object of the invention is to provide an interbody fusion device whereby enough lateral exposure is present to place two large devices side-by-side to distract the disc space and facilitate fusion.

It is yet another object of the invention to provide an interbody fusion device which can be placed closer to another interbody fusion device and which will require no or minimal resection of facet joints.

Yet a further object of the present invention is to provide an implant system which is placed in the intervertebral space with minimal retraction of the spinal cord to lessen the chance of neurological complications or damage.

Other objects and benefits of the present invention can be discerned from the following written description and accompanying figures.

DESCRIPTION OF THE FIGURES

FIG. 1 is a top elevational view of a osteogenic fusion device in accordance with one embodiment of the present invention.

FIG. 2 is an end elevational view of one end of the osteogenic fusion device shown in FIG. 1.

FIG. 3 is a top elevational view of an alternative embodiment of the osteogenic fusion device utilizing exterior threads.

FIG. 4 is a top cross-sectional view of a osteogenic fusion device as shown in FIG. 1 with a bone growth-inducing material supported by the osteogenic fusion device.

FIG. 5 is an cross-sectional view of the osteogenic fusion device and bone growth material shown in FIG. 4 taken along line 5-5 as viewed in the direction of the arrows.

FIG. 6 is a plan view of a sheet for a bone growth-inducing material used with the osteogenic fusion device shown in FIG. 4.

FIG. 7 is an end elevational view of one end of a osteogenic fusion device, such as the osteogenic fusion device of FIG. 1, modified to include apertures.

FIG. 8 is an end elevational view of one end of a osteogenic fusion device, such as the osteogenic fusion device of FIG. 1, modified to include apertures.

FIG. 34 is a top elevational view of an alternative embodiment of the implant system of the present invention.

FIG. 35 is an end elevational view of one end of the implant system depicted in FIG. 34.

FIG. 36 is an end elevational view of the other end of the implant system depicted in FIG. 35.

FIG. 37 is an end elevational view of an alternative embodiment of the implant system of the present invention.

FIG. 38 is a perspective view of an alternative embodiment of the implant system of the present invention.

FIG. 39 is a perspective view of yet a further alternative embodiment of the implant system of the present invention.

DESCRIPTION OF THE PREFERRED EMBODIMENTS

Figure 9:
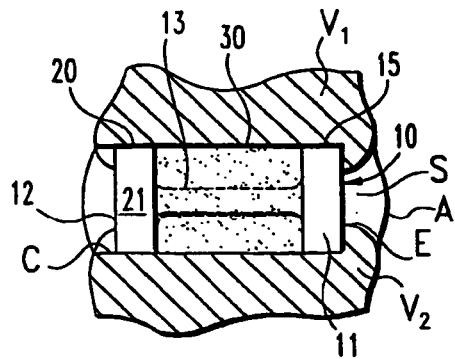
FIG. 9 is a side, partially cross-sectional view of an intervertebral disc space with a osteogenic fusion device according to FIG. 1 implanted between adjacent vertebrae.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention contemplates osteogenic fusion devices for use as interbody fusion devices. The osteogenic fusion devices include opposite end pieces that are configured to span the intervertebral disc space and engage the adjacent vertebral bodies. The inventive osteogenic fusion devices include a central element separating the two end pieces and substantially spanning the anterior-posterior length of the disc space. The invention further contemplates that a bone growth-inducing material be disposed about the central element and between the opposite end pieces. When the inventive osteogenic fusion device is implanted within a patient, the bone growth-inducing material is in direct contact with the adjacent vertebral bodies. The end pieces are formed of a material sufficient to withstand the spinal loads generated at the instrumented vertebral level.

In accordance with one embodiment of the invention, a osteogenic fusion device 10, depicted in FIGS. 1-2, includes a first end piece 11 and a second end piece 12. The end pieces are separated by a central element 13. The first end piece 11 could be substantially cylindrical or any geometrical shape and includes an outer bone contacting surface 15. The end piece 11 also defines an inwardly facing retaining surface 17. The central element 13 integrally extends from the retaining surface 17 of the first end piece 11.

The second end piece 12 also defines a bone contacting surface 20 that, in this embodiment, does not extend entirely around the end piece. The bone contacting surface 20 could be any geometrical shape, preferably circular and is defined at a radius equal to the radius of the outer surface 15 of the first end piece. Thus, as depicted in FIG. 2, the bone contacting surface 20 of the second end piece 12 is generally coincident with portions of the outer surface 15 of the first end piece 11 when the osteogenic fusion device is viewed along the longitudinal axis of its central element 13. The second end piece 12 also includes opposite truncated surfaces 21 that are disposed between the circular bone contacting surfaces 20. Preferably, the truncated surfaces 21 are generally flat and can be configured to be engaged by an insertion tool. The insertion tool preferably has arms that contact the flat truncated surfaces 21, yet still fall within the envelope defined by the outer surface 15 of the first end piece 11.

The second end piece 12 also defines a second retaining surface 22 that faces the first retaining surface 17 of the first end piece 11. Again, the central element 13 is preferably integral with and projects outwardly from the second retaining surface 22.

Alternatively, the central element can be in the form of a central rod that is engaged within colinear bores formed in the two end pieces. In this variation, the engagement between the central rod and the end pieces can be threaded.

The central element 13 includes an outer central surface 23. Preferably, the central element 13 is substantially cylindrical along its length. In one aspect of the invention, the first end piece 11 defines a diameter $D_1$, while the central element 13 defines a diameter $D_2$. The diameter $D_1$ is at least equal to the height of the intervertebral space within which the osteogenic fusion device 10 is to be interposed. Most preferably, the diameter $D_1$-corresponds to the diameter of a cylindrical channel cut into the endplates of the adjacent vertebrae. In this instance, the diameter $D_1$ will be somewhat larger than the intervertebral disc space height. Moreover, the diameter $D_1$ is significantly larger than the diameter $D_2$ of the central element 13. This diameter differential creates an annular pocket 24 surrounding the central element 13.

The osteogenic fusion device 10 has a length $L_1$ between the opposite ends of the osteogenic fusion device. This length $L_1$ is preferably selected to be slightly less than the anterior-posterior length of the intervertebral disc space, although the length can be calibrated to the lateral dimension of the space. Most preferably, the length $L_1$ is sized so that the first and second end pieces 11, 12 can contact at least a portion of the apophysis or harder cortical bone at the perimeter of the vertebral endplates. The osteogenic fusion device 10 further defines a length $L_2$ which is essentially the length of the central element 13. The length $L_2$ is calibrated so that the end pieces 11 and 12 are sufficiently wide to provide adequate support between the adjacent vertebrae. Conversely, the length $L_2$ is sufficiently long so that the annular pocket 24 has the capacity for retaining a substantial quantity of bone growth-inducing material.

In a modification of the osteogenic fusion device 10, the second end piece can be configured with threads. For example, as depicted in FIG. 3 an end piece 25 includes external bone engaging threads 26 extending from the outer surface 27. In accordance with this embodiment, the second end piece 25 can be cylindrical, like the first end piece 11, or the threads can be formed between truncated surfaces, such as truncated surfaces 21 in the prior embodiment. At any rate, the threaded end piece 25 is configured to be threadedly advanced into a drilled and tapped channel within the adjacent vertebral bodies. The first end piece 11 can also be threaded to facilitate insertion and to reduce the chance of expulsion.

In a further aspect of the invention, a bone growth-inducing material 30 is provided for support by the osteogenic fusion device 10. Preferably the material 30 is in the form of a sheet. In a specific example, the carrier sheet 30 can be a collagen sheet that is soaked with a solution containing a bone growth-inducing substance, or a bone morphogenetic protein (BMP).

In accordance with the invention, the carrier sheet 30 can be formed of a variety of materials other than collagen, provided the materials are capable of containing a therapeutically effective quantity of a bone growth-inducing substance or BMP. Moreover, the material 30, whether in sheet form or not, is most preferably susceptible to manipulation to be disposed within the annular pocket 24 of the fusion device 10.

In accordance with the specific embodiment, the carrier sheet 30 is wound around the outer surface 23 of the central element 13 (see FIG. 5). The carrier sheet 30 is held between the retaining surface 17 of the first end piece 11 and the retaining surface 22 of the second end piece 12. In accordance with one specific embodiment, the retaining surface 22 is curved or convex. In this way, the carrier sheet 30 can project into the convexity to serve as a sort of anchor to hold the carrier sheet 30 within the annular pocket 24 of the osteogenic fusion device 10. In addition, the convex surface 22 conforms better with the anterior portion of the vertebral body profile when the fusion device is implanted.

In the illustrated embodiment, the carrier sheet 30 can be provided as a single sheet, as shown in FIG. 6. The inner end 31 of the sheet is disposed against the central outer surface 23 of the central element 13. The sheet can be wound in a spiral fashion about the central element 13 until its outer end 32 is disposed adjacent the outer surface 15 of the first end piece 11. The carrier sheet 30 has width W that is preferably slightly larger than the length $L_2$ between the first and second end pieces to allow a portion of the carrier sheet 30 to project into the concave retaining surface 22 of the second end piece 12. The overall length of the sheet 30 between ends 31 and 32 depends upon its thickness and the difference in diameters $D_1$ and $D_2$. For example, in one embodiment the diameter $D_2$ is about one-fourth (¼) the diameter $D_1$. Preferably, the length is sufficient so that the carrier sheet 30 can be, tightly wound about the central element 13 and fill the annular pocket 24. One important object of the present invention is that the carrier sheet 30 or bone growth-inducing material reside in direct contact with the adjacent vertebral bone. Consequently, the sheet 30 is preferably wound so that its outer end 32 is at least slightly outside the envelope of the outer surface 15 of the first end piece 11.

The carrier sheet 30 of FIGS. 4-6 illustrates one specific embodiment of bone growth-inducing material usable with the osteogenic fusion device of the present invention. It is also contemplated that the carrier can be in the form of a sponge, paste, gel or a settable osteogenic material. The osteogenic material must be provided in some form that can be generally retained about the central element 13 and within the annular pocket 24 of the osteogenic fusion device 10. Put differently, the present invention contemplates an osteogenic material that does not need to be contained in the traditional manner of the hollow cylindrical cages of the prior art. In these prior art devices, cancellous bone chips have been contained within a hollow cage. The present invention does not contemplate the use of bone chips alone. However, bone chips contained within a bone paste or a gel may be utilized with the osteogenic fusion device 10, provided that the paste or gel have a consistency sufficient to hold the bone, growth-inducing material on and within the osteogenic fusion device 10.

In accordance with one specific embodiment, the end pieces 11 and 12 are solid and circular in configuration. Alternative end piece configurations are shown in FIGS. 7 and 8. For example, end piece 11' can have a plurality of generally circular apertures 34 disposed circumferentially about the end piece, as shown in FIG. 7. The end piece 11" shown in FIG. 8 includes a plurality of pie-shaped apertures 35 so that the end piece gives the appearance of a spoked wheel. The second end piece 12 of the osteogenic fusion device 10 can have similar apertures defined therethrough. The apertures 34 and 35 in the end pieces 11", 11" provide a further avenue for facilitating fusion bone growth. The apertures themselves can be filled with a osteogenic material, such as a gel or a paste. Moreover, once the osteogenic fusion device 10 is implanted within an intervertebral disc space, osteogenic material can be packed around the osteogenic fusion device within the disc space. These additional apertures in the end pieces 11, 12 provide further avenues for the formation of a bony bridge between adjacent vertebrae.

The end pieces 11,12, etc. can also have non-circular shapes. For instance, the end pieces can be rectangular or other multi-sided shapes. If the osteogenic fusion device resides within a channel prepared in the endplates, the channel shape can be modified to conform to the bone engaging surfaces 15, 20 of the end pieces.

Figure 10:
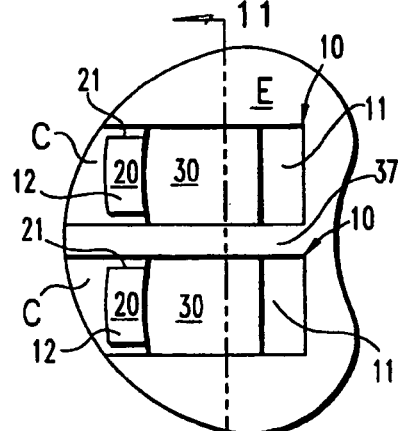
FIG. 10 is a top elevational view of the superior aspect of the instrumented vertebral level shown in FIG. 9, depicting bilateral placement of osteogenic fusion devices according to the present invention.
Figure 11:
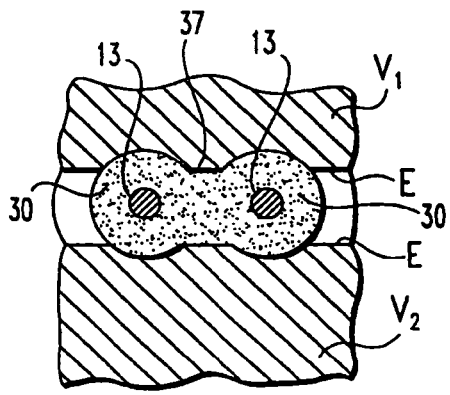
FIG. 11 is a cross-sectional view of the instrumented vertebral segment shown in FIG. 10, taken along line 11-11 as viewed in the direction of the arrows.

FIGS. 9-11 depict a pair of osteogenic fusion devices 10 implanted in a bi-lateral configuration between adjacent vertebral bodies $V_1$ and $V_2$. As depicted, the disc annulus A is retained but at least one portal must be defined in the annulus A to permit insertion of the osteogenic fusion devices 10. The present invention also contemplates insertion of each osteogenic fusion device 10 through its own portal formed in the disc annulus A. Alternatively, in conformance with other known procedures, a single portal can be provided through which each osteogenic fusion device 10 is successively inserted. Further in accordance with the present invention, the osteogenic fusion devices 10 can be positioned within the intervertebral disc space according to known posterior or postero-lateral techniques.

According to the present invention, the osteogenic fusion device 10 is inserted into the disc space S with the first end piece 11 proceeding first into the space. Preferably, a channel C is bored into the vertebral endplates E to a preferred depth of insertion of the osteogenic fusion device 10, in accordance with known techniques. If the osteogenic fusion device to be implanted is of the type shown in FIG. 3 with the threaded second end piece 25, the channels C can be appropriately drilled and tapped to accommodate the bone engaging threads 26. In a modification of this embodiment, the first end piece 11 can also carry external threads.

The preferred embodiment contemplates a generally cylindrical osteogenic fusion device placed within circular channels. Alternatively, the osteogenic fusion devices can operate as spacers that directly contact the endplates, without a prepared channel. In this instance, the bone engaging surfaces of the end pieces can be modified to conform to the vertebral endplate geometry.

As depicted in FIGS. 9-11, the osteogenic material 30 is disposed in direct contact with the adjacent vertebral endplates E. Moreover, the placement of osteogenic fusion devices 10 can present a medial space 37 between the two osteogenic fusion devices. Osteogenic material can then be placed within the medial space 37, again in direct contact with the osteogenic material 30 situated around the central elements 13 of each of the osteogenic fusion devices 10. Once complete fusion occurs, new bone growth will substitute the carrier material 30 to form a solid bony bridge spanning the adjacent vertebrae $V_1$, $V_2$. As can be seen from FIGS. 9-11, the region of continuous bone growth is very substantial and is not interrupted by the structure of the fusion device itself.

It is understood, of course, that the end pieces 11 and 12 provide sufficient support for the vertebral loads passing between the adjacent vertebrae. At the same time, this load bearing capacity is concentrated outside the middle regions of the vertebral endplates E. It is known that the central region of the endplates is very rich in blood flow and has a high capacity for new bone growth. Thus, the elimination of structural material of the osteogenic fusion device 10 from that region provides for a faster and more complete arthrodesis than may have been possible with prior fusion cages.

Figures 14, 15:
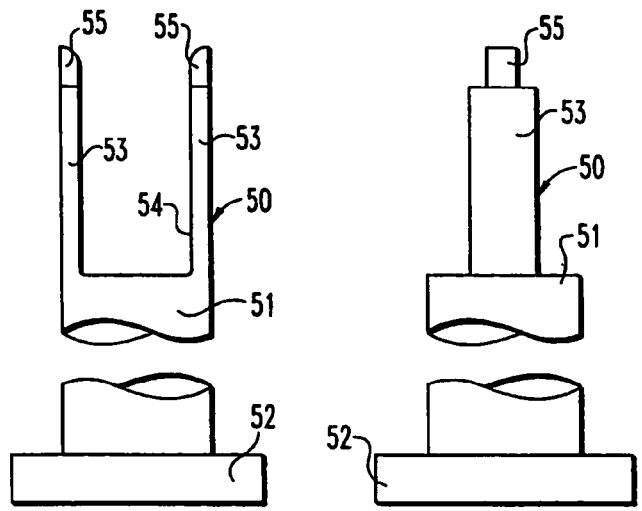
FIG. 14 is a side elevational view of an insertion tool according to one embodiment of the present invention.
FIG. 15 is a top elevational view of the insertion tool shown in FIG. 14.

Referring next to FIGS. 14, 15, an insertion tool 50 is depicted for inserting a osteogenic fusion device 10 according to the present invention. The insertion tool 50 includes a solid shank 51 to which a knob or handle 52 is affixed. The knob 52 is configured for manual grasping and manipulation during insertion of the osteogenic fusion device. In the case where the osteogenic fusion device is not threaded, the insertion tool 50 simply acts as a pushing device. On the other hand, in the instance where the osteogenic fusion device includes threaded end pieces such as shown in FIG. 3, the insertion tool 50 must be rotated as the end piece is threaded into the prepared channel between the adjacent endplates.

The insertion tool 50 includes a pair of prongs 53 that are disposed apart to define an end piece recess 54. For insertion of the osteogenic fusion device 10 shown in FIG. 1, the end piece recess 54 is configured so that the prongs 53 are in tight contact with the truncated surfaces 21 of the second end piece 12. The outer surface of the prongs 53 can conform to a portion of the outer surface 15 of the first end piece 11.

Figures 12, 13:
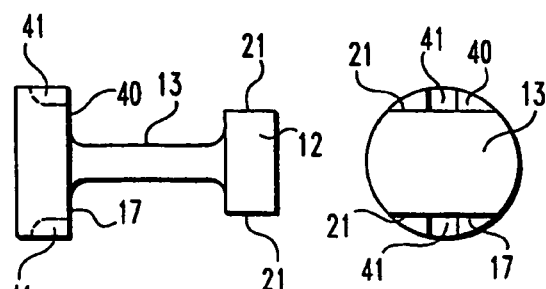
FIG. 12 is a top elevational view of a osteogenic fusion device, such as shown in FIG. 1, with features to permit insertion of the osteogenic fusion device.
FIG. 13 is an end elevational view of the osteogenic fusion device shown in FIG. 12.

The insertion tool 50 depicted in FIGS. 14-15 also includes tapered tips 55 at the ends of each of the prongs 53. These tapered tips are configured to be received within driving notches 41 in a modified first end piece 40, as depicted in FIGS. 12-13. The osteogenic fusion device depicted in FIGS. 12-13 is substantially similar to the osteogenic fusion device 10 shown in FIG. 1, with the exception of the added driving notches. The insertion tool 50 is configured so that the tips 55 project into the notches 41 while the prongs 53 directly contact the truncated surfaces 21 of the second end piece 12. This particular configuration of the insertion tool is particularly useful for threaded insertion of the osteogenic fusion device. Preferably, the prongs 53 have an effective outer diameter that is approximately equal to the diameter $D_1$. Moreover, the prongs 53 can have an arc segment configuration to complement the truncated surfaces 21. If the end piece 12 is threaded (see FIG. 3), the prongs 53 can include complementary threads along their length.

Figure 16:
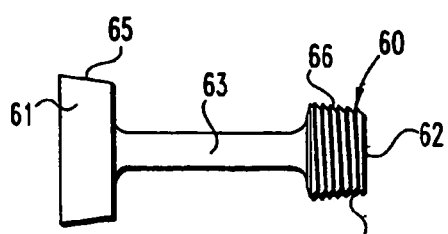
FIG. 16 is a top elevational view of a osteogenic fusion device for restoring the lordotic angle between adjacent vertebrae according to a further embodiment of the present invention.

The present invention also contemplates a osteogenic fusion device for restoring the normal lordotic angle of an intervertebral segment. Specifically, a lordotic osteogenic fusion device 60 includes a first end piece 61 and a second end piece 62 as shown in FIG. 16. As with the prior embodiments, a central element 63 is provided to connect the two end pieces. The outer surface 65 of the first end piece 61 is in the form of a frusto-conical surface. The outer surface 65 tapers toward the second end piece 62 at a preferred lordotic angle. Similarly, the outer surface 66 of the second end piece 62 is also tapered at a similar lordotic angle. Alternatively, the second end piece 62 can include threads formed on the outer surface 66. While the threads 66 at the smaller second end piece 62 may not contact the vertebral endplates at the larger insertion end, the threads will contact the endplates at the anterior end of the intradiscal space and will act as an anchor to resist expulsion of the lordotic osteogenic fusion device 60.

Figure 17:
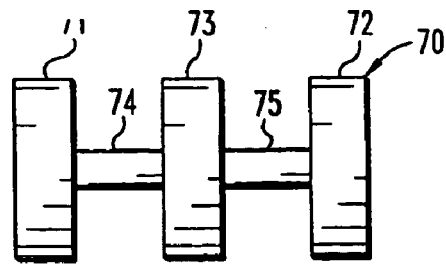
FIG. 17 is a top elevational view of a osteogenic fusion device according to a further embodiment of the present invention.

The present invention contemplates several modifications to the basic osteogenic fusion device 10. For example, the osteogenic fusion device 70 shown in FIG. 17 includes first and second end pieces 71, 72 and a center piece 73 disposed between the two end pieces. First and second central elements 74 and 75 connect each of the end pieces 71, 72 to the center piece 73. In this instance, the center piece 73 will contact the interior of the disc endplates E. Osteogenic material, such as carrier sheets 30, can be disposed or wound around each of the central elements 74, 75 until the end of the bone growth-inducing material is exposed at the outer surface of the osteogenic fusion device 70.

Figure 18:
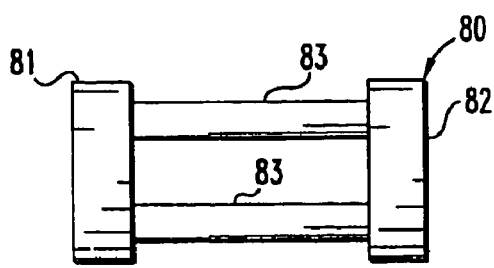
FIG. 18 is a top elevational view of a osteogenic fusion device according to a still further embodiment of the present invention.
Figure 19:
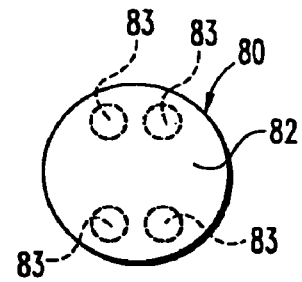
FIG. 19 is an end elevational view of the osteogenic fusion device shown in FIG. 18.

In a further modification, a osteogenic fusion device 80 depicted in FIG. 18 includes first and second end pieces 81 and 82 that are connected by a plurality of central beams 83. In the illustrated embodiment as shown in FIG. 19, four such beams 83 are provided; however, other arrangements and numbers of beams are contemplated. Important aspects of the present invention are retained by the osteogenic fusion device 80 because osteogenic material can be supported by the several beams 83 between the first and second end pieces 81, 82, with the bone growth-inducing material in direct contact with the adjacent vertebral bodies.

Figure 20:
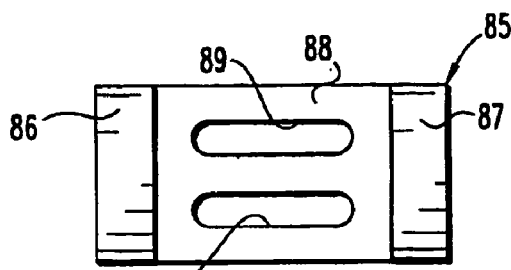
FIG. 20 is a top elevational view of a osteogenic fusion device according to another embodiment of the present invention.
Figure 21:
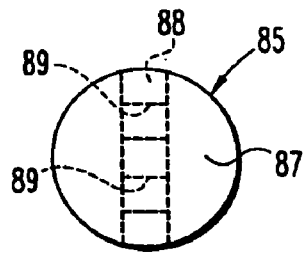
FIG. 21 is an end elevational view of the osteogenic fusion device shown in FIG. 20.

The two embodiments of FIGS. 20-21 and FIGS. 22-23 pose a slight deviation from the general concept of the osteogenic fusion device 10. In these two embodiments, the smaller diameter central element 13 is replaced by a wall. In the embodiment of FIGS. 20-21, a osteogenic fusion device 85 includes first and second ends 86, 87 separated by a central element 88. The first and second ends 86 and 87 can be in the form of short cylindrical sections, such as the first end piece 11 of the osteogenic fusion device 10 in FIG. 1. While the central element 88 can be in the form of a solid wall, the osteogenic fusion device 85 preferably includes a number of slots 89 defined through the central element 88. In accordance with the specific embodiment, the slots extend along substantially the entire length of the central element 88. While the osteogenic fusion device 85 deviates somewhat from the concept of the osteogenic fusion device 10, this latter osteogenic fusion device 85 retains the broad beneficial feature of the present invention, namely provision for direct contact between osteogenic material supported by the osteogenic fusion device 85 and the vertebral endplates. In the present instance, the osteogenic material can be situated on opposite sides of the central element 88. In addition, the material can be passed through the slots 89.

Preferably, the osteogenic fusion device 85 will be oriented within the intervertebral disc space with the central element 88, or wall, spanning between the adjacent vertebrae. This central element 88, then, will provide additional structure and load bearing capability for sustaining the spinal loads at the instrumented level.

Figure 22:
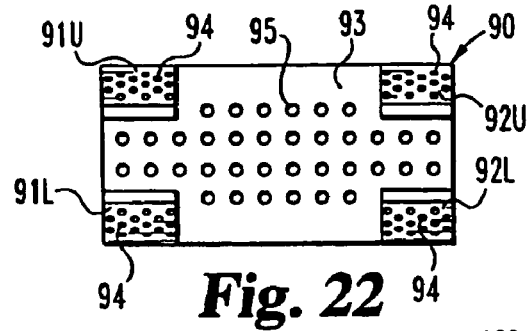
FIG. 22 is a top elevational view of a osteogenic fusion device according to yet another embodiment of the present invention.
Figure 23:
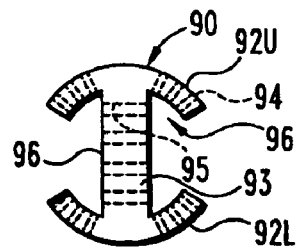
FIG. 23 is an end elevational view of the osteogenic fusion device shown in FIG. 22.

The osteogenic fusion device 90 of FIGS. 22-23 operates on a similar concept to the osteogenic fusion device 85. However, in this instance, the first and second end pieces are in the form of arc segments, rather than shortened cylinders. Specifically, the osteogenic fusion device 90 includes upper and lower first arc segments $91_U$ and $91_L$, and upper and lower second arc segments $92_U$ and $92_L$. The osteogenic fusion device 90 also includes a central element 93 that is again in the form of a wall connecting the first and second end pieces. As can be seen most clearly in FIG. 23, the arc segments 91, 92 and central element 93 define a pair of cavities 96 for containing osteogenic material. In this embodiment, the osteogenic material can be contained completely from end to end of the osteogenic fusion device 90. In the prior embodiments, the osteogenic material is contained within retaining surfaces of the opposite end pieces. In accordance with a specific embodiment, the osteogenic fusion device 90 includes a plurality of apertures 94 defined in each of the upper and lower first and second arc segments $91_U$, $91_L$, $92_U$ and $92_L$. Similarly, a plurality of apertures 95 can be defined through the central element 93. In this manner, the apertures provide the maximum capacity for bone ingrowth not only around, but also through the osteogenic fusion device 90.

Figure 24:
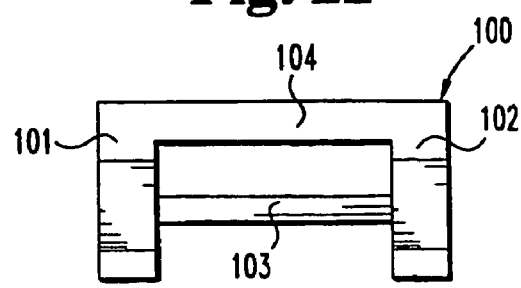
FIG. 24 is a top elevational view of a osteogenic fusion device according to a further embodiment of the present invention.
Figure 25:
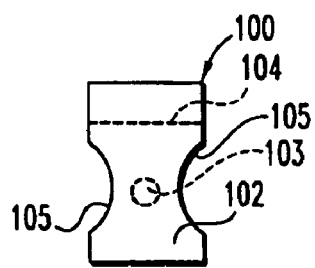
FIG. 25 is an end elevational view of the osteogenic fusion device shown in FIG. 25.
Figure 26:
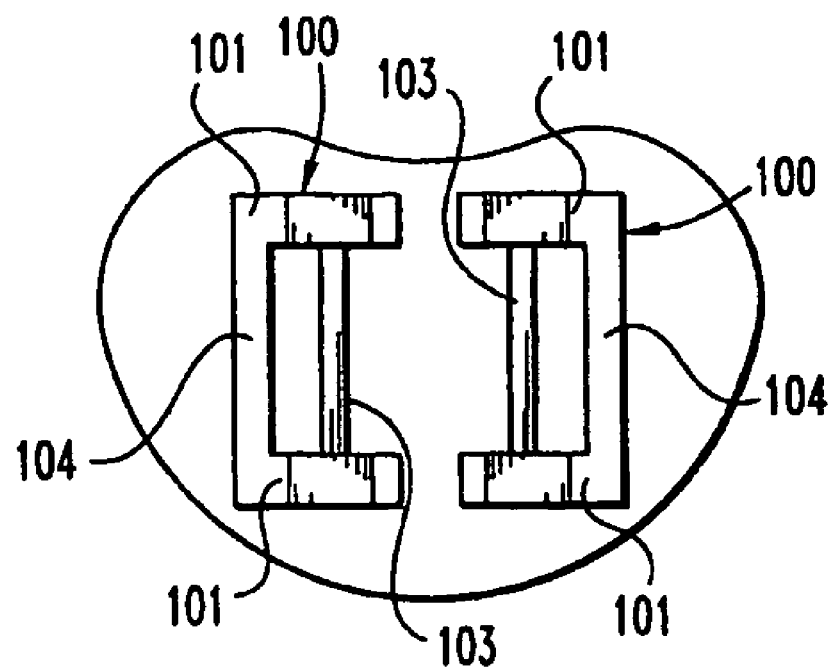
FIG. 26 is a top elevational view of a pair of fusion devices according to FIGS. 24-25 disposed in a bilateral configuration in the lumbar spine.
Figure 27:
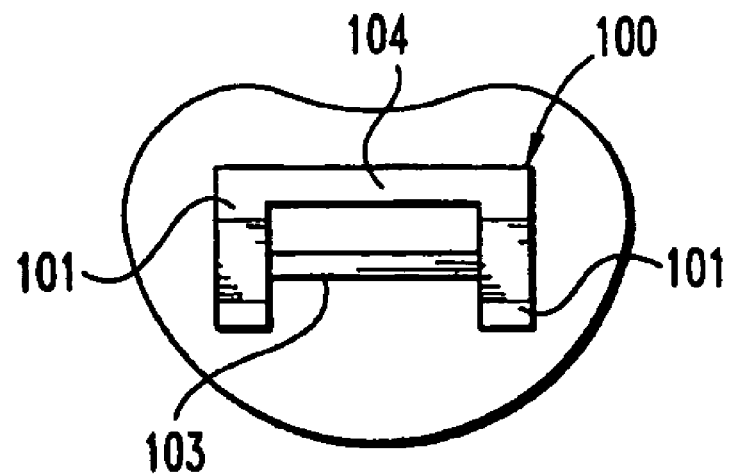
FIG. 27 is a top elevational view of a fusion device according to FIGS. 24-25 disposed in the cervical spine.

A osteogenic fusion device 100 shown in FIGS. 24-25 again presents a slightly different concept. This osteogenic fusion device 100 includes a first end plate 101, a second end plate 102 and a central element 103 that are similar to the like-named components of the osteogenic fusion device 10. However, the osteogenic fusion device 100 also includes a side piece 104 spanning between the first and second end pieces 101, 102. Moreover, unlike the osteogenic fusion device 10, the first and second end pieces 101, 102 are not generally circular in configuration, but are—WO 99/2027119 PCT/US98/26254 generally rectangular in configuration. In one specific embodiment, the end pieces 101, 102 can include cutouts 105 at opposite sides of the end pieces to provide further avenues for the formation of a bony bridge between adjacent vertebrae. As with the prior embodiments, the osteogenic fusion device 100 provides means for adequately containing osteogenic material, such as in the form of the carrier sheet 30. In this embodiment, the carrier sheet 30 can be wound around the central element 103, in the manner described above. This particular embodiment of the invention, namely osteogenic fusion device 100, is preferably adapted for use in the lumbar spine as illustrated in FIG. 26 and in the cervical spine illustrated in FIG. 27, and is consequently sized accordingly.

Figure 28:
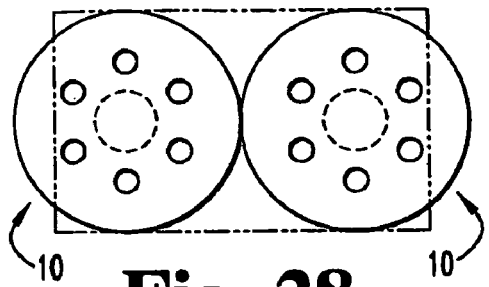
FIG. 28 is an end elevational view of osteogenic fusion devices of the present invention within a surgical window showing how such fusion devices of particular sizes may not fit entirely within the surgical window.

In many situations, it is preferable to use two fusion devices in a posterior lumbar interbody fusion technique (PLIF) but there is not enough lateral exposure to place two devices side-by-side. This problem can be visualized, for example, by reference to FIG. 28. Two osteogenic fusion devices, such as osteogenic fusion device 10, may be placed side-by-side within a surgical window depicted by the dotted line. As seen in FIG. 28, the two devices do not fit within the surgical window presented. In many such cases, the facet joints must be removed to make the surgical window larger, which may lead to spinal instability.

Figure 29:
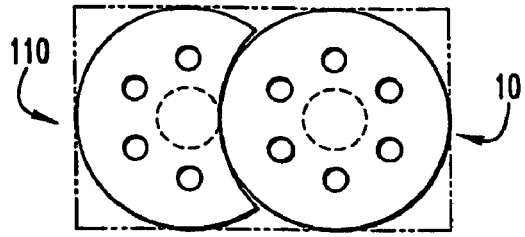
FIG. 29 is an end elevational view similar to that of FIG. 28 and depicting one embodiment of the implant system of the present invention.

In order to address this problem, at least one end piece of an osteogenic fusion device may have a truncated surface, such as a circular cutout, as depicted in FIG. 29. As seen in FIG. 29, two fusion devices placed together thereby nest or interleave and reside within the operative window, and thus require no or minimal resection of the facet joints.

Figure 30:
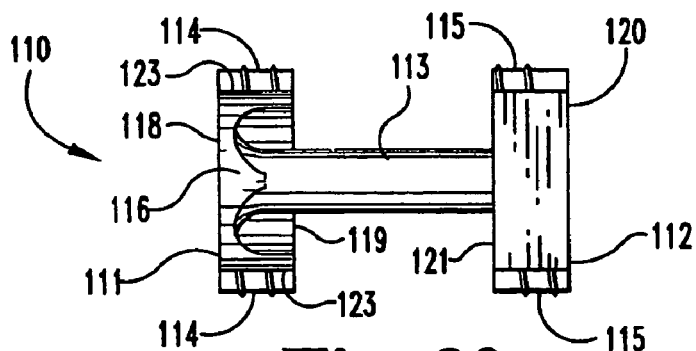
FIG. 30 is a side elevational view of a osteogenic fusion device in accordance with an alternative embodiment of the present invention.
Figure 31:
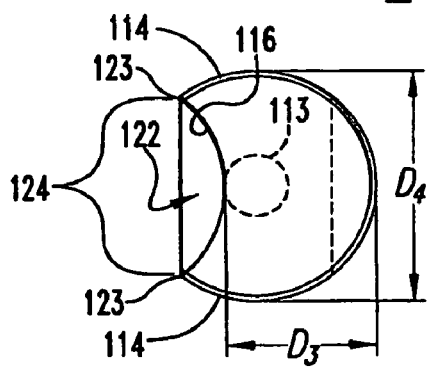
FIG. 31 is an end elevational view of one end of the osteogenic fusion device shown in FIG. 30.
Figure 32:
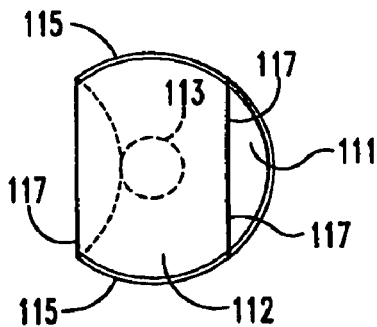
FIG. 32 is an end elevational view of the other end of the osteogenic fusion device depicted in FIG. 31.

As more fully shown in FIGS. 30-32, osteogenic fusion device 110 is in many respects similar to osteogenic fusion device 10 depicted in FIGS. 1 and 2 and includes, for example, opposite end pieces including first end piece 111 and second end piece 112 and central element 113. Each end piece defines two opposing surfaces as similarly described for osteogenic fusion device 10. For example, first end piece 111 defines a bone contacting surface 114 and second end piece 112 defines a bone contacting surface 115. Bone contacting surface 115, in this embodiment, does not extend entirely around end piece 112. Moreover, the bone contacting surface of second end piece 112 is generally coincident with portions of the outer surface 114 of first end piece 111 when the device is viewed along the longitudinal axis of its central element 13. Second end piece 112 also includes two opposite truncated surfaces 117 that are disposed between bone contacting surfaces 115. Additionally, first end piece 111 includes external face 118 and internal face 119 whereas second end piece 112 includes external face 120 and internal face 121. Osteogenic fusion device 110 is configured to nest with another osteogenic fusion device, including other devices of the present invention. In the embodiment depicted in FIGS. 30-32, the configuration of the osteogenic fusion device 110 includes a first end piece 111 having opposite faces, including opposite edges 123, that define an entrance 124 to a cutout region 122. Cutout region 122 is defined by truncated surface 116. Truncated surface 116, in this embodiment, is concave. As best seen in FIG. 31, first end piece 111 has a minimum lateral dimension $D_3$ transverse to a maximum vertical dimension $D_4$ between the two opposite surfaces 114. In the illustrated device, maximum vertical dimension $D_4$ is generally larger than minimum lateral dimension $D_3$. Vertical dimension $D_4$ has a height approximating the desired separation of the adjacent vertebrae.

Figure 33:
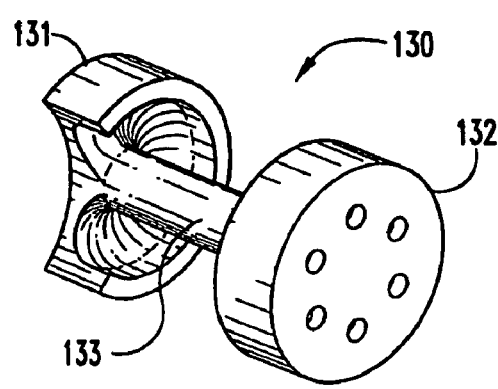
FIG. 33 is a perspective view of an alternative embodiment of the osteogenic fusion device of the present invention.

FIG. 33 depicts another embodiment, in which load bearing member 130 has a first end piece 131 with a truncation adapted for nesting and a second generally cylindrical end piece 132 having no cutout regions.

The above-described osteogenic fusion devices configured to nest may also bear modifications similar to those shown in FIGS. 3-13 and 16-21, and their accompanying descriptions in the text above. For example, osteogenic fusion devices having threaded end pieces, end pieces with apertures, and such devices having either center pieces, a plurality of central elements and a central element defining a wall may also be incorporated into osteogenic fusion devices such as those described in conjunction with FIGS. 30-33. In devices with center pieces, the center pieces may be substantially cylindrical with no cutout regions or may be shaped with a cutout region as described above. Moreover, the device can also include a bone growth-inducing material as described above which may be wound around the central elements of the devices, and if desired also shaped to allow for or facilitate the nesting arrangement.

It is to be noted that the shapes of the opposing end pieces of the load bearing members described above are preferably cylindrical and may include a concave truncated surface. However, opposite end pieces and truncated surfaces having any suitable geometrical shape are contemplated as forming a part of the present invention.

The present invention also contemplates an implant system including at least two load bearing members as described above and wherein at least one load bearing member is configured to nest within the other load bearing member. FIGS. 34-36 depict one embodiment of the implant system including load bearing member 110 and load bearing member 10 (as shown in FIGS. 1 and 2) having a substantially cylindrical first end piece 11. First end piece 11 of load bearing member 10 is nested within first end piece 111 of load bearing member 110. In this particular embodiment as best seen in FIG. 36, width $w_1$ of second end piece 112 of load bearing member 110 and width $w_2$ of second end piece 12 of load bearing member 10, when added together, must be such that will not prevent first end piece 11 of load bearing member 10 from nesting within first end piece 111 of first load bearing member 110.

In yet a further embodiment, the load bearing members in a nesting implant system may have an identical shape. For example, FIG. 37 depicts a perspective view of two load bearing members 110 wherein first end piece 111 of one of the load bearing members is nested within an identical end piece 111 of the other load bearing member 110.

FIG. 38 shows implant system 150 of the invention which includes load bearing member 160 and load bearing member 170. Load bearing member 160 is similar to load bearing member 130 except that second end piece 162 of load bearing member 160 is substantially cylindrical with a cutout portion (i.e., it has the shape of first end piece 131 of load bearing member 130). Load bearing member 170 is similar to load bearing member 130 except that first end piece 171 of load bearing member 170 is substantially cylindrical, with no cutout regions. FIG. 38 further depicts first end piece 171 of load bearing member 170 nested within first end piece 161 of load bearing member 160 and second end piece 172 of load bearing member 170 is nested within second end piece 162 of load bearing member 160.

It is to be appreciated that the implant system may include first and second load bearing members with end pieces arranged in a variety of ways to achieve the nesting arrangement. For example, the first and second load bearing members may each include one truncated and one non-truncated end piece, such as that illustrated in FIG. 33. In such an embodiment, the two devices can be used in inverted relationship with respect to one another to achieve a nesting relationship. For example, in implant system 180 shown in FIG. 39, first end piece 191 of first load bearing member 190 and second end piece 202 of second load bearing member 200 are truncated. Nontruncated first end piece 201 of load bearing member 200 is nested within first end piece 191 of load bearing member 190 and non-truncated second end piece 192 of load bearing member 190 is nested within second end piece 202 of second load bearing member 200.

Figure 40:
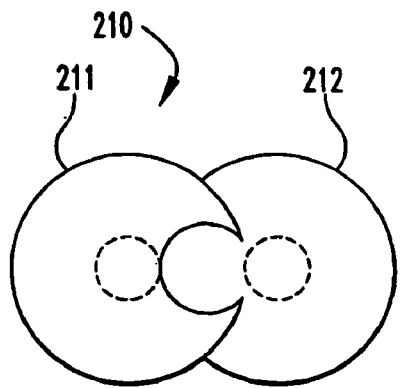
FIG. 40 is an end elevational view of mated osteogenic fusion devices of the invention.
Figure 41:
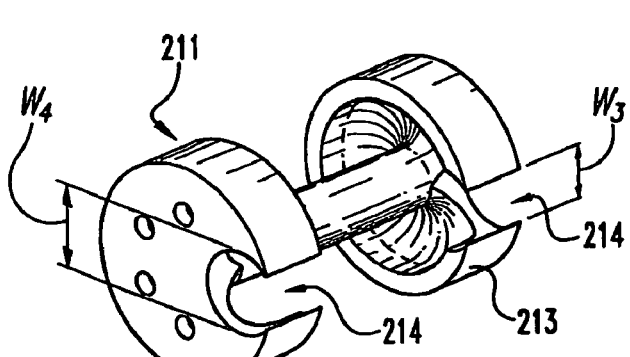
FIG. 41 is a perspective view of one of the osteogenic fusion devices depicted in FIG. 40.
Figure 42:
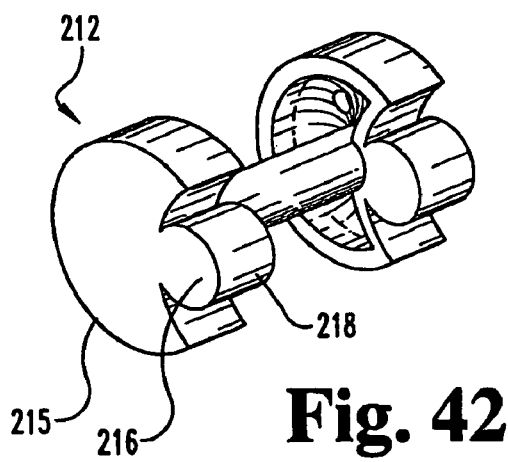
FIG. 42 is a perspective view of another of the osteogenic fusion devices depicted in FIG. 40.
Figure 43:
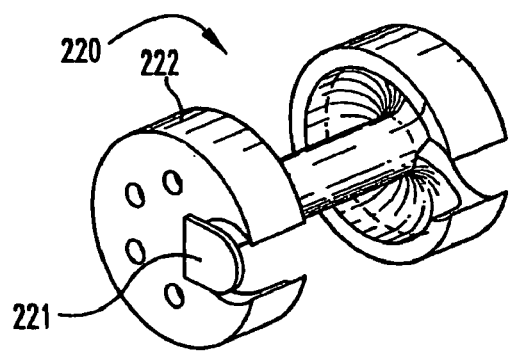
FIG. 43 is a perspective view of an osteogenic fusion device of the invention including a stop member.

With reference now to FIGS. 40-42, shown is an implant system of the invention including mated fusion devices and wherein the devices are configured to connect to one another so as to resist lateral separation of the devices. In preferred systems, such connection may also provide increased resistance to expulsion due to the cooperation of the two devices. In particular, the system 210 includes a first fusion device 211 and a second fusion device 212. First fusion device 211 includes end pieces 213 having openings 214 serving as female members. Second fusion device 212 includes end pieces 215 having mating members 216 sized correspondingly to fit within openings 214 of device 212 and serve as male members. In this fashion, when devices 211 and 212 are assembled as depicted in FIG. 40, the two devices are connectedly mated so as to resist lateral separation from one another and/or expulsion, desirably acting more as a single unit when implanted in a patient. In this regard, devices 211 and 212 may be mated prior to implantation and implanted as a single unit: however, it is contemplated as preferred to implant a first of the devices, e.g. device 211, and then to implant the second device, e.g. 212, by pushing or sliding the second device in next to the first implanted device along the long axis, such that mating members 216 are received within openings 214 thus connecting the two devices to one another. As illustrated, devices 211 and 212 are also configured to nest to present a reduced lateral profile generally as described above for certain devices. Thus, device 212 includes concave shoulder portions 217, with mating member 216 located therebetween with its outward end 218 extending radially outward to a distance which allows the nesting relationship. In device 212, outward end 218 extends radially outward no further than the radius r of the predominant cylindrical shape of end piece 215. Devices 211 and 212 can optionally have outer surfaces configured to resist expulsion from the space between adjacent vertebrae, for example threads, ratchets, grooves or other like features. In one mode, one of the fusion devices may include threads that facilitate controlled insertion, and that device may be implanted first. The other fusion device of the system can be of the push-in type, having no expulsion-resisting features or those features commonly used for push-in devices, for example ratchets or similar protuberances, or grooves. Still further, at least one of the fusion devices can include a stop member to controllably stop insertion of the second device by contact between the two devices. For example, illustrated in FIG. 43 is a device 220 similar to device 211, except including a stop member 221 positioned to be contacted by mating member 216 of device 212, for example in a procedure in which device 220 is implanted first with end piece 222 occurring distally, and device 212 is thereafter pushed in and mated with device 220.

Figure 44:
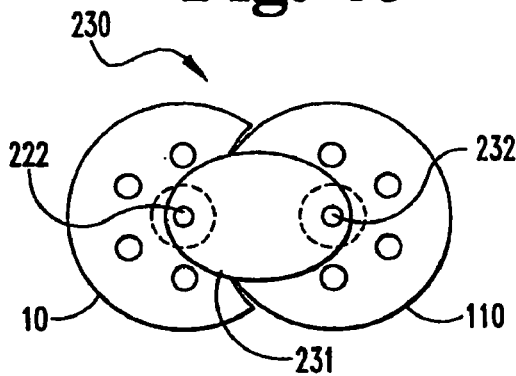
FIG. 44 is an end elevational view of mated osteogenic fusion devices connected by a connecting plate in accordance with the invention.

With reference now to FIG. 44, illustrated in another implant system of the invention in which two adjacent fusion devices are connected to one another. In particular, system 230 includes a first fusion device 10 and a second fusion device 110 as described above. In addition, system 230 includes a relatively thin connecting plate 231 spanning the end pieces of devices 10 and 110. Connectors 232, for example screws, pins or the like, extend through plate 231 and into the end pieces of devices 10 and 110. In this case, such end pieces can include corresponding means for receiving connectors 232, for example a threaded hole in the case where connectors 232 are screws. Implant system 230 having devices 10 and 110 connected in this fashion at one or both ends will thus also desirably act more as a single unit within the patient, desirably adding torsional resistance. It is contemplated that the devices 10 and 110 may be connected prior to or after implant. In one mode, for example, devices 10 and 110 may be implanted separately in the nested relationship, and only a single plate 231 used to connect the proximal (more accessible) end pieces.

Use of two large devices side-by-side in accordance with the invention facilitates engagement of the devices into the vertebral body endplates to distract the disc space and facilitate fusion. The larger diameter devices provide other advantages over the use of two small diameter devices. For example, the deeper the devices are placed into the endplates, the more bleeding bone is exposed and the better the chance for new bone formation. Moreover, the smaller diameter devices do not get adequate distraction or stabilization in the end plate bone allowing for motion which inhibits new bone formation. The larger diameter devices are advantageously used in situations requiring less lateral exposure to implant two devices side-by-side (i.e., bilaterally).

The design of the above-described devices that have cylindrical end pieces with cutout regions can be used in current fusion cages that act as containers, or baskets, for holding autograft chips and in allograft bone dowels. Such a design allows for threading-in of the devices much closer together as desired for a PLIF procedure. Moreover, the instruments that indicate the correct vertical orientation of the cage for bone thru-growth can also assist in orienting the cage cutout on the medial side for mating with a second cage.

The present invention contemplates osteogenic fusion devices that are formed of a material that is sufficiently strong to support the adjacent vertebrae and to maintain the disc height of the instrumented intervertebral space. For example, the osteogenic fusion devices, such as osteogenic fusion device 10, can be formed of a biocompatible sterilizable metal, such as stainless steel or titanium. Of course, other medical grade materials are contemplated, such as certain ceramics, polymers, etc., as well as allograft and xenograft bone, provided the materials are sufficiently strong. The overall dimensions of each of the osteogenic fusion devices described above depends upon the instrumented level. For example, a osteogenic fusion device for use in the cervical spine must necessarily be smaller than a osteogenic fusion device used in the lumbar spine. Moreover, the relative dimensions of the components of the osteogenic fusion devices may be altered depending upon the vertebral level to be instrumented. For example, a osteogenic fusion device, such as osteogenic fusion device 10, for use in the lumbar spine, may require a central element 13 having a diameter $D_2$ that is more than one fourth of the outer diameter $D_1$ of the outer surface 15 of the first end piece 11. In some instances, the lumbar spine may generate bending moments across a osteogenic fusion device, such as osteogenic fusion device 10, that would require a stronger central element 13.

In accordance with the present invention, the illustrated osteogenic fusion devices can be of the push-in or threaded-in type. Of course, the end pieces, such as end pieces 11, 12 of osteogenic fusion device 10, and end pieces 111, 112 of osteogenic fusion device 110, can include various surface characteristics known in the art for enhancing the degree of fixation of the osteogenic fusion device between the adjacent vertebrae. For example, the end pieces can include certain macro surface features for penetrating the vertebral endplates to resist expulsion of the osteogenic fusion devices. Likewise, the surfaces, such as outer surface 15 and 114 and bone contacting surface 20 and 115 can be provided with bone ingrowth coatings so that a certain amount of bone ingrowth occurs even between the end pieces and the adjacent vertebral bodies.

The present invention also provides a method of promoting fusion bone growth in the space between adjacent vertebrae. The method advantageously includes providing the load bearing members or implant systems described above, preparing adjacent vertebrae to receive the load bearing member or implant system and placing the load bearing member or implant system into the intervertebral space after the preparing step. The load bearing members and implant system may also include an osteogenic material within the pocket of the devices that is arranged to contact the adjacent vertebrae when the vertebrae are supported by the opposite end pieces of the device as described more fully above.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A spinal implant for insertion into a space between adjacent vertebrae, comprising:
    an elongated central element extending along a longitudinal axis wherein said elongated central element comprises a solid rod;
    opposite first and second pieces including opposing inwardly facing surfaces, said central element extending axially between and attached to central portions of said inwardly facing surfaces, at least one of said first and second end pieces including an outer perimeter extending about said longitudinal axis, said outer perimeter defining a circular region and a recessed region;
    wherein each of said first and second end pieces includes a plurality of radially extending spokes extending radially outward from said central portion and defining triangular-shaped apertures therebetween to facilitate bone growth into said annular pocket; and
    wherein said central element defines a first outer dimension transverse to said longitudinal axis, said first and second end pieces defining a second outer dimension transverse to said longitudinal axis, said first outer dimension of said central element being less than said second outer dimension of said first and second end pieces to define an annular pocket surrounding and extending continuously about said central element and extending between said inwardly facing surfaces of said first and second end pieces.

2. The spinal implant of claim 1, wherein each of said first and second end pieces includes an outer perimeter defining a circular region and a recessed region.

3. The spinal implant of claim 1, wherein at least one of said first and second end pieces has a non-circular shape.

4. The spinal implant of claim 1, wherein said first and second end pieces are formed integral with said central element to define a single-piece implant structure.

5. The spinal implant of claim 1, further comprising a bone growth-inducing material positioned within said annular pocket and between said first and second end pieces.

6. The spinal implant of claim 1, wherein said first and second end pieces are configured to bear against the adjacent vertebrae to maintain a height between the adjacent vertebra.

7. The spinal implant of claim 1, wherein said first outer dimension of said central element is no more than about 25% of said second outer dimension of said first and second end pieces.

8. A spinal implant for insertion into a space between adjacent vertebra, comprising:
- an elongated central element extending along a longitudinal axis wherein said elongated central element comprises a solid rod;
- opposite first and second pieces including opposing inwardly facing surfaces, said central element extending axially between and attached to central portions of said inwardly facing surfaces at least one of said first and second end pieces including an outer perimeter extending about said longitudinal axis, said outer perimeter defining a circular region and a recessed region; and
- wherein at least one of said first and second end pieces includes an outer perimeter defining a non-circular shape; and
- wherein each of said first and second end pieces has a circular region and a recessed region; and
- wherein said central element defines a first outer dimension transverse to said longitudinal axis, said first and second end pieces defining a second outer dimension transverse to said longitudinal axis, said first outer dimension of said central element being less than said second outer dimension of said first and second end pieces to define an annular pocket surrounding and extending continuously about said central element and extending between said inwardly facing surfaces of said first and second end pieces; and
- a bone growth-inducing material positioned within said annular pocket between said first and second end pieces.

9. The spinal implant of claim 8, wherein said bone growth-inducing material extends annularly about said central element.

10. The spinal implant of claim 9, wherein said bone growth-inducing material extends entirely about said central element.

11. The spinal implant of claim 8, wherein said bone growth-inducing material comprises an osteogenic material.

12. The spinal implant of claim 8, wherein each of said first and second end pieces includes a plurality of radially extending spoke extending radially outward from said central portion and defining triangular-shaped apertures therebetween to facilitate bone growth into said annular pocket.

13. The spinal implant of claim 8, wherein said first and second end pieces are formed integral with said central element to define a single-piece implant structure.

14. The spinal implant of claim 8, wherein said first and second end pieces each define a bone engaging surface configured to bear against an adjacent vertebra to maintain a height between the adjacent vertebrae.

15. The spinal implant of claim 8, wherein said first outer dimension of said central element is no more than about 25% of said second outer dimension of said first and second end pieces.

* * * * *